United States Patent [19]

Szebenyi nee Györi et al.

[11] 4,233,121
[45] Nov. 11, 1980

[54] PROCESS FOR THE PREPARATION OF 5-HALO-6,9 α-OXIDO-PROSTAGLANDIN DERIVATIVES

[75] Inventors: Enikö Szebenyi nee Györi,

[73] Assignee: Chinoin Gyógyszer és Vegyészeti Termékek Gyára R.T., Budapest, Hungary

[21] Appl. No.: 41,104

[22] Filed: May 21, 1979

[30] Foreign Application Priority Data

May 29, 1978 [HU] Hungary .................. CI1832

[51] Int. Cl.³ .................. C25B 3/02; C25B 3/06; C07D 307/77
[52] U.S. Cl. .................. 204/59 R; 204/72; 204/78; 204/79; 204/81; 260/346.22
[58] Field of Search .................. 204/59 R, 72, 78, 79, 204/81

[56] References Cited

U.S. PATENT DOCUMENTS 3,427,235  2/1969  Le Duc .................. 204/78
4,125,712  11/1978  Axen .................. 260/346.22 X

FOREIGN PATENT DOCUMENTS 851122  8/1977  Belgium .

OTHER PUBLICATIONS

Chem. Biochem., and Pharmacological Activity of Prostanoids, Roberts et al., p. 290, pub. by Pergamon, N.Y., 1979.
Mech. of Oxidation of Org. Cpds. by Waters, pp. 49-51, pub. by Methuen, London, 1964.
Intro. to Org. Electrochem, by Rifi et al., 1974, pp. 282, 298-307, pub. by Marcel Dekker, New York.
Tamoskozi et al., Tetrahedron Letters, 1977, pp. 2627, 2628.

*Primary Examiner*—F. Edmundson
*Attorney, Agent, or Firm*—Karl F. Ross

[57] ABSTRACT

The invention concerns a new process for the preparation of 5-halo-6,9α-oxido-prostaglandin derivatives of the general formula II

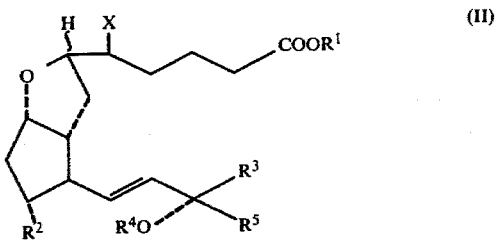

wherein
$R^1$ represents a hydrogen atom, an alkyl group optionally substituted by aryl, amino, hydroxyl or a halogen atom, an equivalent of a pharmaceutically acceptable organic or inorganic cation or a conventional hydroxyl protecting group;
$R^2$ represents a hydrogen atom, a hydroxyl group or a conventionally protected hydroxyl group;
$R^3$ is a hydrogen atom or a lower alkyl group;
$R^4$ represents a hydrogen atom or a conventional hydroxyl protecting group;
$R^5$ stands for a straight or branched chained alkyl group, optionally containing hetero atom(s) and optionally substituted by a substituted or unsubstituted aryl group, and
X stands for a halogen atom, which comprises subjecting prostaglandin $F_{2\alpha}$ derivatives of the general formula I

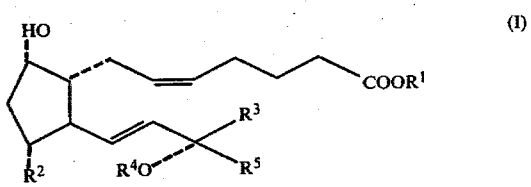

15 Claims, 1 Drawing Figure

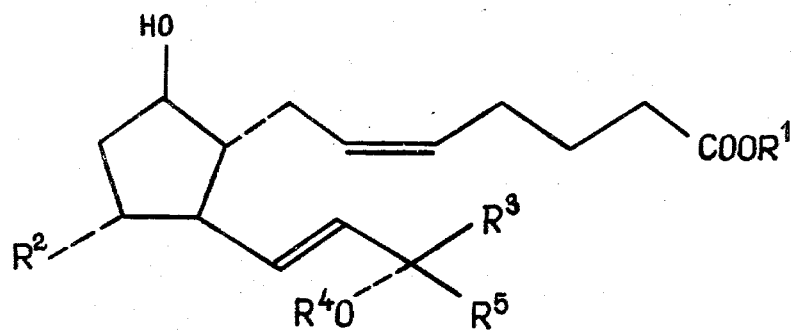
I.
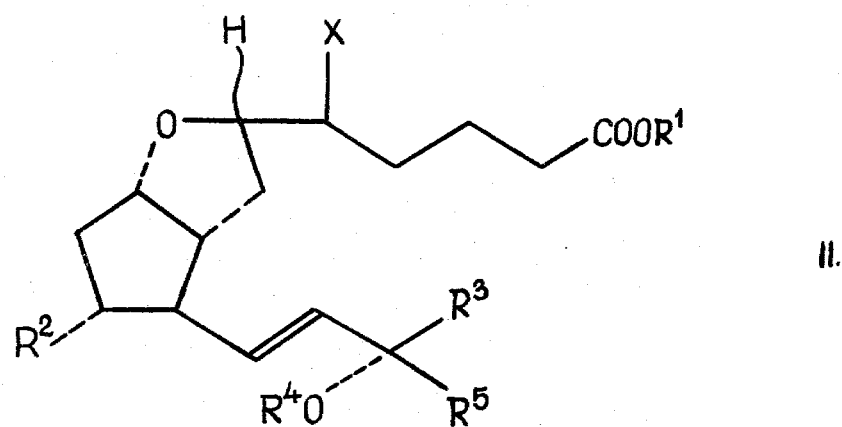
II.
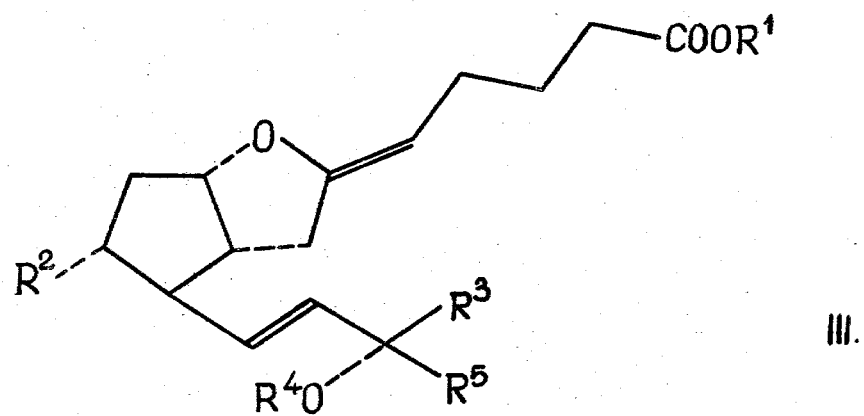
III.

PROCESS FOR THE PREPARATION OF 5-HALO-6,9 α-OXIDO-PROSTAGLANDIN DERIVATIVES

The present invention relates to a new electro-chemical process for the preparation of 5-halo-6,9α-oxido-prostaglandin derivatives of the formula II

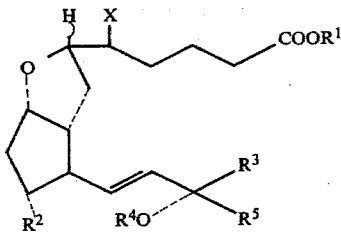

wherein $R^1$ is hydrogen alkyl which can be substituted by aryl, amino, hydroxyl or halogen an equivalent of a pharmaceutically acceptable organic or inorganic cation or a conventional hydroxyl protecting group;

$R^2$ is hydrogen, a hydroxyl group or a conventionally protected hydroxyl group;

$R^3$ is hydrogen atom or lower alkyl group;

$R^4$ is hydrogen or conventional hydroxyl protecting group;

$R^5$ is straight or branched chain alkyl which can contain one or more heteroatoms or be substituted with a substituted or unsubstituted aryl group, and X is halogen.

According to the invention compounds of the formula II are prepared by subjecting prostaglandin $F_{2\alpha}$ derivatives of the formula I

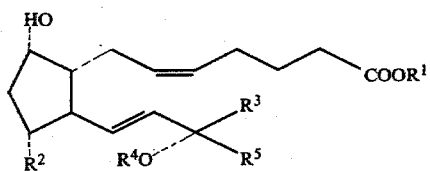

to electro chemical oxidation in a halide ion-containing medium.

In the definition of $R^1$ and $R^5$ the term "alkyl" is intended to include both straight and branched chained hydrocarbons having from 1 to 20 carbon atoms. The preferred $R^1$ alkyl groups contain from 1 to 4 or from 8 to 10 carbon atoms. The lower carbon chain facilitates an optional isolation following the reaction, while the longer carbon chain is advantageous because the metabolysis of those prostacyclin derivatives of the formula III

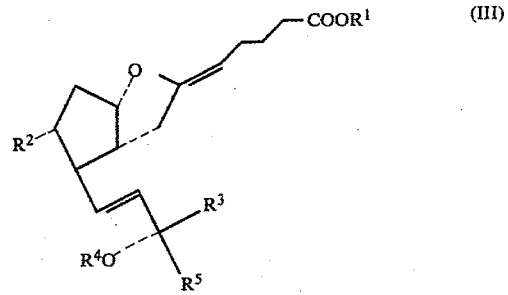

prepared by the dehydrohalogenation of 5-halo-6,9α-oxido-prostaglandin derivatives of the formula II, which have a longer $R^1$ alkyl chain is slower. If $R^5$ represents an unsubstituted alkyl group, the alkyl chain preferably contains five carbon atoms. The lower alkyl groups contain from 1 to 4 carbon atoms. Preferred representatives of lower alkyls are methyl, ethyl, n- and isopropyl, and n-, iso-, sec.- and tertiary butyl groups.

The pharmaceutically acceptable organic and inorganic cations include cations which are not toxic in doses in which prostacyclins are generally administered. Preferred inorganic cations include alkali metal and alkaline-earth metal cations, but $R^1$ can stand also for an equivalent of aluminum, iron or any other non-toxic cation. Preferred organic cations include cations derived from various primary, secondary or tertiary alkylamines, arylamines or aralkylamines and from heterocyclic amines. The solubility and crystallizability of the compounds of the formula II, are considerably increased when said cations are substituted, for example by hydroxyl groups.

As hydroxyl protecting groups all groups conventionally used for this purpose in the chemistry of prostaglandins can be used. Typical representatives are: tetrahydropyranyl, various alkylsilyl, aromatic and aliphatic acyl or aromatic carbamoyl groups. The protecting groups, if any, can be eliminated after the electro chemical oxidation, for example by hydrolysis.

5-halo-6,9α-oxido-prostaglandin derivatives of the general formula II are valuable intermediates in the synthesis of prostacyclin derivatives of the general formula III $R^2$, $R^3$, $R^4$ and $R^5$ are as defined above, which have anti-coagulant activity.

Methods for the preparation of prostacyclin derivatives starting from prostaglandin derivatives of the formula II, in which X is iodine are known in the art [Tetrahedron Letters 30, 2627 (1977) and Belgian Pat. No. 851122]. According to the known methods prostaglandin $F_{2\alpha}$ or a derivative thereof is reacted with a suitable electrophillic reactant to prepare a corresponding 6,9α-oxido-prostaglandin derivative of the formula II, which can subsequently be transformed into a corresponding prostacyclin derivative.

It has surprisingly been found that prostaglandin $F_{2\alpha}$ derivatives of the formula I can be converted into the corresponding 5-halo-6,9α-oxido-prostaglandin derivatives of the formula II by electro chemical oxidation, in a medium which contains halide ions, without using any chemical oxidant. The electro chemical oxidation is easy to control, and the reaction proceeds quickly and much easier than earlier methods known for this purpose. In addition to its simplicity a further advantage of the electro chemical process according to the invention is that it can easily be carried out continuously, in suitably chosen electrolytic cell, and therefore is suitable for a large-scale application. Since no chemical oxidizing agent is required for this reaction, also additional reaction steps like elimination of the excess of oxidating agent and of the by-products derived from the decomposition thereof is unnecessary, and the halogenation is easy to control by the suitable regulation of the parameters of electrolysis.

In this way the velocity of halogenation and the quantity of the halogen used can be controlled effectively. A further advantage consists in the fact that the reaction can be regulated by electrical parameters, which can be measured directly, with high accuracy.

Prostaglandin $F_{2\alpha}$ derivatives of the formula I, used as starting compounds in the reaction according to the invention are known in the art, and are widely used in human and veterinary therapy, primarily for the treatment of female patients.

Electro chemical halogenation according to the invention is performed in a medium containing halide ions. Halide ions are introduced into the electrolyte in the form of suitable salts. For this purpose halides are used which are soluble in the reaction medium. Preferred representatives of these halides are alkali metal and alkali-earth metal iodides and bromides but iodide and bromide salts of organic cations can also be used. Due to their good availability and other advantageous properties especially alkali metal iodides and bromides, e.g. sodium, potassium and lithium iodides and bromides are advantageously used for this purpose. Since these salts are readily soluble in the reaction mixture and dissociate therein, they also play the role of a so-called "conducting salt".

The reaction mixture is neutral or slightly acidic. As a solvent protic and aprotic polar solvents or mixtures thereof can be used. Preferred solvents are water, alcohols, nitriles, more preferably lower alkanols and/or nitriles, organic or inorganic acids. The electrolyte can also contain various salts, for example, as buffers.

The electro chemical oxidation can be carried out at a temperature between 0° C. and 80° C., preferably at room temperature, by using anodes having a large oxygen overvoltage. Suitable anodes are for example gold, platinum, palladium and titanium. The electrolysis is preferably carried out in an electrolytic cell in which cathode and anode are separated by a diaphragm, to inhibit the admixture of the electrolyte. As a diaphragm for example a glass filter, a ceramic plate or an ion-exchanging membrane can be used. The electrolysis is preferably performed with an anodic current density of 0.1 to 10 $A/dm^2$. It is very favorable that halogen substitution and ring closure according to the invention are completed within 5 to 10 minutes by contrast with the method described in the Belgian Pat. No. 851122, in which iodine substitution and ring closure carried out chemically take 2 to 3 hours. It has been found that for the electro chemical iodination according to the invention about 120 % of the theoretical charge is required. Halogenation may conveniently be monitored by thin layer chromatography (t.l.c.).

During the electro chemical halogenation the $\Delta^5$-cis-double bond of the compounds of the formula I is substituted regioselectively, through an intermediate of the onium ion type to give compounds of the formula II. It is the 9α-hydroxyl group of said compound of the formula I which participates in the substitution reaction.

The electro chemical halogenation according to the invention results in the formation of two isomers of the compounds of the formula II. The isomers obtained are epimers with respect to the configuration of the 6-hydrogen (exo-endo isomers), wherein reference is made to the numbering conventional in the chemistry of prostaglandins. The ratio of the exo epimer to the endo epimer may be varied between 1:1 to 1:10, depending on the electrolytic parameters, i. e. electrolyte concentration, quality of the anode, current density, temperature, electrolyte composition. The epimers obtained can be separated by column chromatography carried out on silica gel. Preferably ester derivatives of the formula II, in which $R^1$ represents an alkyl group are subjected to chromatography. If the compounds of the formula II are intended to be used for the preparation of prostacyclin derivatives of the formula III, the epimers generally need not be separated, since dehydrohalogenation of either of the epimers of the formula II provides the same prostacyclin derivative.

Figure 1:
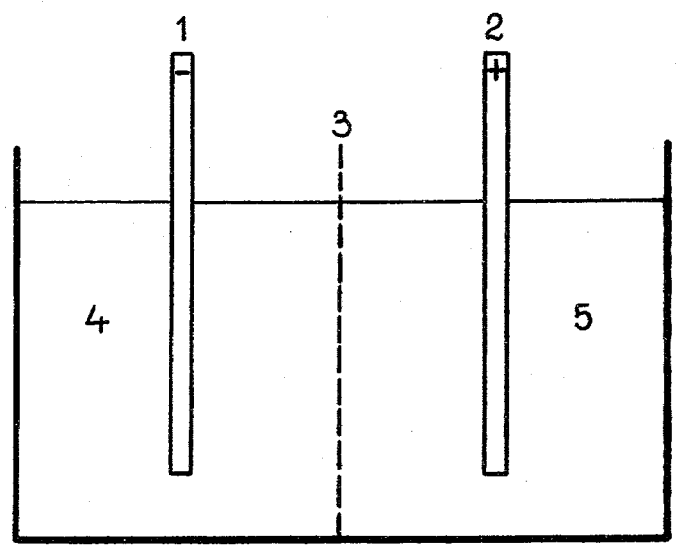
FIG. 1 of the drawing is a diagrammatic cross section through an electrolytic cell, for carrying out the process of the invention.

Further details of the invention are to be found in the following, non-limiting examples.

EXAMPLE 1

An electrolytic cell is prepared according to the setup illustrated on FIG. 1. If the reaction is to be carried out at a temperature different from room temperature, the electrolytic cell is thermostated in a conventional way. The thermostating jacket is not illustrated in the FIGURE. In the electrolytic apparatus shown in FIG. 1 cathode 1 is dipped into the cathode space 4, while anode 2 is dipped into the anode space 5. The two electrode spaces are separated from each other by diaphragm 3. As a cathode a platinum spiral having an area of 4 $cm^2$, as an anode a platinum plate of 10 $cm^2$ is employed. The catholyte consists of 10 ml. of distilled water, 100 mg. (1 mmole) of potassium acetate, 0.6 ml. (1 mmole) of a 96 % aqueous acetic acid solution and 100 mg. (0.6 mmoles) of potassium iodide. The components listed above form a clear solution when admixed. The anolyte has the same composition as the catholyte except that it also contains 150 mg. (0.4 mmoles) of prostaglandin $F_{2\alpha}$.

When the cell is ready and filled with the electrolytes, the anodic current density is adjusted to 6 $A/dm^2$, and the electrolysis is continued at 25° C. for about 7 minutes. The terminal voltage is 25 V. The termination of the reaction is indicated by a sudden increase in the terminal voltage of the cell.

The dark brown anolyte obtained as a result of the electrolysis is extracted with 20 ml. of ether, the ethereal extract is washed with 0.5 ml. of a 10 % sodium thiosulphate solution and subsequently with four 5 ml. portions of water, and finally dried over anhydrous magnesium sulphate, at 0° C., in darkness. The solution is then evaporated and acetic acid is eliminated under a pressure of 1 mmHg until a steady weight is achieved. As a residue 180 mg. (88 %) of 5-iodine-6,9α-oxido-11α,15α--dihydroxy-13-trans-prostenic acid are obtained. According to t.l.c. analysis the product is an approximately 5:1 mixture of endo- and exo-epimers. T.l.c. measurements are carried out on silica gel, using a 20:10:1 mixture of benzene, dioxane and acetic acid. The spots obtained are identified by means of chemically pure and stereouniform 6-endo-5α-iodine-6,9α-oxido-11α,15α-dihydroxy-13-trans-prostenic acid, prepared by a chemical method [Tetrahedron Letters 30, 2627 (1977)] which was previously identified by different methods. In the above system $R_f$ for the 6-endo isomer amounts to 0.25, while the 6-exo isomer has an $R_f$-value of 0.30.

6-endo-5α-iodine-6,9α-oxido-11α,15α-dihydroxy-13-trans-prostenic acid and 6-exo-isomer thereof are esterified by diazomethane in a manner known per se.
$R_f$(6-endo methylester): 0.40;
$R_f$(6-exo methylester): 0.43.

EXAMPLE 2

The electrolytic cell is essentially identical with that used in Example 1, with the only difference that as an anode a platinum plate of 0.5 cm² area is used.

The catholyte consists of 10 ml. of acetonitrile, 50 mg. (0.4 mmoles) of potassium bromide, 0.5 ml. of water and 0.25 ml. of acetic acid. The anolyte in addition to the above components contains 50 mg. (0.15 mmoles) of prostaglandin $F_{2\alpha}$.

Electrolysis is performed with an anodic current density of 0.6 A/dm² for 20 minutes. The terminal voltage of the cell is of about 2 to 3 V.

When the electrolysis is complete the solvent is evaporated from the anolite under reduced pressure to give 75 mg. of a crude product, which is a 5:1 mixture of 6-endo-6,9α-oxido-5α-bromo-11α,15α-dihydroxy-13-trans-prostenic acid and 6-exo-6,9α-oxido-5α-bromo-11α,15α-dihydroxy-13-trans-prostenic acid and contains a small amount of more and less polar impurities. T.l.c. measurement is carried out as described in Example 1.
$R_f$(endo isomer): 0.22;
$R_f$(exo isomer): 0.27.

The crude product is converted into the corresponding methyl ester with diazomethane in a manner known per se.
$R_f$(endo methyl ester): 0.35;
$R_f$(exo methyl ester): 0.41.

The t.l.c. spots are identified by means of chemically pure and stereouniform corresponding endo- and exo compounds of the formula II, which had been prepared chemically [Tetrahedron Letters, 30, 2627 (1977)], and were identified by different known methods.

What we claim is:
1. A process for the preparation of a 5-halo-6,9α-oxido-prostaglandin derivative of the formula II

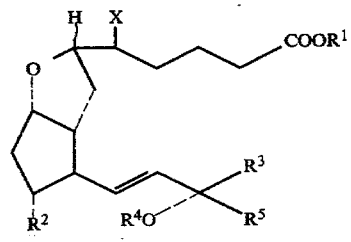

wherein
  $R^1$ is hydrogen alkyl which can be substituted with aryl, amino, hydroxyl or halogen, a pharmaceutically acceptable organic or inorganic cation or a conventional hydroxyl protecting group;
  $R^2$ is hydrogen hydroxyl or a conventionally protected hydroxyl group;
  $R^3$ is hydrogen or lower alkyl;
  $R^4$ is hydrogen or a conventional hydroxyl protecting group;
  $R^5$ is straight or branched chain alkyl, which can contain one or more heteroatoms and which can be substituted with a substituted or unsubstituted aryl group, and
  X is halogen,
which comprises subjecting a prostaglandin $F_{2\alpha}$ derivative of the formula I

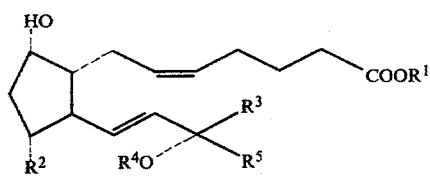

to electrochemical oxidation in a protic medium containing halide ions.

2. The process defined in claim 1 wherein the electrochemical oxidation is carried out in a medium containing water, alkanols, nitriles, organic or inorganic acids or mixtures thereof as a protic solvent, which can contain salts acting as a buffer.

3. The process defined in claim 2, in which as a protic solvent a lower alkanol, nitrile or a mixture thereof is used.

4. The process defined in claim 1 for the preparation of a compound of the formula II, wherein X is iodine, which comprises carrying out the electrochemical oxidation in a medium containing water, acetic acid, an alkali metal acetate, and an alkali metal iodide.

5. The process defined in claim 1 for the preparation of 5-iodo-6,9α-oxido-11α,15α-dihydroxy-13-trans-prostenic acid, which comprises subjecting prostaglandin $F_{2\alpha}$ to electrochemical oxidation in a medium containing iodine ions.

6. The process defined in claim 1 for the preparation of a compound of the formula II, in which X is bromine which comprises carrying out the electrochemical oxidation in a medium containing water, acetonitrile, acetic acid and an alkali metal bromide.

7. The process defined in claim 1 for the preparation of 5-bromo-6,9α-, 15α-dihydroxy-13-trans-prostenic acid, which comprises subjecting prostaglandin $F_{2\alpha}$ to electrochemical oxidation in a medium containing bromide ions.

8. The process defined in claim 1 which comprises carrying out the electrochemical oxidation in an electrolytic cell, in which the cathode and anode space are separated by a diaphragm.

9. The process as defined in claim 1 which comprises carrying out the electrochemical oxidation by using as an anode an electrode having a high oxygen overvoltage.

10. The process as defined in claim 9, in which as an anode having a high oxygen overvoltage, gold, platinum, palladium or titanium is employed.

11. The process defined in claim 1 wherein the electrochemical oxidation is carried out at a temperature between 0° C. and 80° C.

12. The process as defined in claim 1 wherein the compound of formula II produced by electrochemical oxidation has one of said protecting groups, said process further comprising splitting off the latter protecting groups.

13. A process as claimed in claim 1, substantially as hereinbefore described with reference to any one of Examples 1 and 2.

14. A process for the preparation of a 5-halo-6,9α-oxido-prostaglandin derivative of the formula

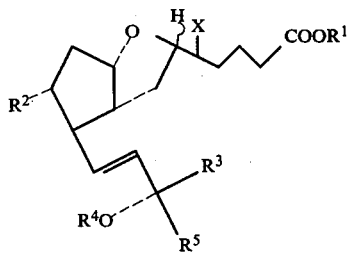

wherein
$R^1$ is hydrogen, $C_1$ to $C_{20}$ straight or branched alkyl which can be substituted with amino, hydroxyl or halogen, or a pharmaceutically acceptable organic or inorganic cation;
$R^2$ is hydrogen or hydroxyl;
$R^3$ is hydrogen or lower alkyl;
$R^4$ is hydrogen;
$R^5$ is straight or branched chain $C_1$ to $C_{20}$ alkyl; and is halogen,
which comprises subjecting a prostaglandin $F_{2\alpha}$ derivative of the formula

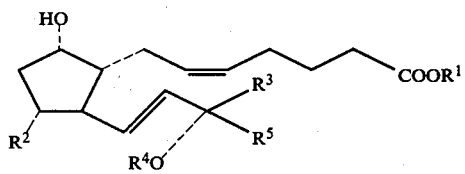

to electrochemical oxidation in an aqueous medium containing ions selected from the group which consist of bromide and iodide.

15. A process for the preparation of a 5-halo-6,9α-oxido-prostaglandin derivative of the formula

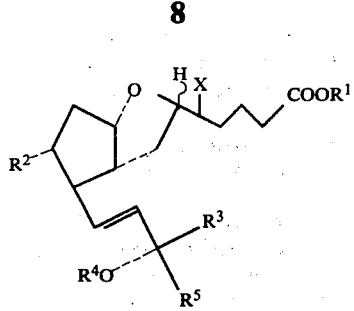

wherein
$R^1$ is hydrogen, $C_1$ to $C_2$ straight or branched alkyl which can be substituted with amino, hydroxyl or halogen, a pharmaceutically acceptable organic or inorganic cation or a hydroxyl protecting group selected from the group which consists of tetrahydro pyranyl, alkylsilyl, aromatic or aliphatic acyl or aromatic carbamoyl eliminated by hydrolysis;
$R^2$ is hydrogen hydroxyl or hydroxyl having a hydroxyl protecting group selected from the group which consists of tetrahydro pyranyl, alkylsilyl, aromatic or aliphatic acyl or aromatic carbamoyl eliminated by hydrolysis;
$R^3$ is hydrogen or lower alkyl;
$R^4$ is hydrogen or a hydroxyl protecting group selected from the group which consists of tetrahydro pyranyl, alkylsilyl, aromatic or aliphatic acyl or aromatic carbamoyl eliminated by hydrolysis;
$R^5$ is straight or branched chain $C_1$ to $C_{20}$ alkyl; and
X is halogen,
which comprises subjecting a prostaglandin $F_{2\alpha}$ derivative of the formula

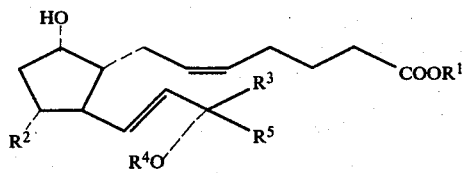

to electrochemical oxidation in an aqueous medium containing ions selected from the group which consists of bromide and iodide.

* * * * *